United States Patent [19]

Laufer et al.

[11] Patent Number: 5,942,535

[45] Date of Patent: *Aug. 24, 1999

[54] [A]-ANNELATED PYRROLE DERIVATIVES AND PHARMACEUTICAL USE THEREOF

[75] Inventors: Stefan Laufer; Hans Günther Striegel, both of Blaubeuren; Gerd Dannhardt, Mainz, all of Germany

[73] Assignee: Merckle GmbH, Blaubeuren, Germany

[*] Notice: This patent is subject to a terminal disclaimer.

[21] Appl. No.: 08/737,921

[22] PCT Filed: May 31, 1995

[86] PCT No.: PCT/EP95/02079

§ 371 Date: Mar. 28, 1997

§ 102(e) Date: Mar. 28, 1997

[87] PCT Pub. No.: WO95/32972

PCT Pub. Date: Dec. 7, 1995

[30] Foreign Application Priority Data

Jun. 1, 1994 [DE] Germany ............................ 44 19 247

[51] Int. Cl.⁶ .................. C07D 487/04; C07D 517/04; C07D 498/04; C07D 471/04; A61K 31/40; A61K 31/425

[52] U.S. Cl. .................. 514/413; 514/256; 514/269; 514/274; 514/312; 514/314; 514/338; 514/339; 514/362; 514/363; 514/365; 514/368; 514/369; 514/374; 514/375; 514/376; 514/393; 514/397; 548/127; 548/128; 548/152; 548/159; 548/170; 548/171; 548/180; 548/204; 548/207; 548/217; 548/236; 548/247; 548/302.7; 548/311.7; 548/312.1; 548/512; 548/513; 548/516; 546/153; 546/155; 546/157; 546/174; 546/175; 546/270.1; 546/271.7; 546/273.1; 546/276.7; 544/242; 544/301; 544/311; 544/312; 544/316; 544/317; 544/319; 544/334; 544/335

[58] Field of Search ...................... 514/256, 269, 514/274, 312, 314, 338, 339, 362, 363, 365, 368, 369, 374, 375, 376, 393, 397, 413; 548/127, 128, 152, 159, 170, 171, 180, 204, 207, 217, 236, 247, 302.7, 311.7, 312.1, 512, 513, 516; 544/242, 301, 311, 312, 316, 317, 319, 334, 335; 546/153, 155, 157, 174, 175, 270.1, 271.7, 273.1, 276.7

[56] References Cited

U.S. PATENT DOCUMENTS

| | | | |
|---|---|---|---|
| 3,920,672 | 11/1975 | Untch et al. ............... | 260/306.7 |
| 4,536,512 | 8/1985 | Biftu et al. ................. | 514/413 |
| 4,539,400 | 9/1985 | Fabre et al. ................ | 544/47 |
| 4,546,100 | 10/1985 | Fabre et al. ................ | 514/231 |
| 4,584,297 | 4/1986 | Fabre et al. ................ | 514/226 |
| 4,684,658 | 8/1987 | Fabre et al. ................ | 514/338 |
| 5,552,422 | 9/1996 | Gauthier et al. ........... | 514/368 |
| 5,631,122 | 5/1997 | Mihayashi et al. ......... | 430/506 |

FOREIGN PATENT DOCUMENTS 0 118 321  9/1984  European Pat. Off. .
0 147 317  7/1985  European Pat. Off. .
0 397 175  11/1990 European Pat. Off. .
2 419 071  11/1974 Germany .

OTHER PUBLICATIONS

Artis et al., "Oxidative Radical Cyclization of (w–Iodoalkyl)indoles and Pyrroles. Synthesis of ( )–Monomorine and Three Diastereomers", Journal of Organic Chemistry, vol. 59, No. 9, pp. 2456–2466, May 1994.

Padwa et al., "Azomethine Ylide Generation via the Dipole Cascade", Tetrahedron, vol. 48, No. 36, pp. 7565–7580, 1992.

Pizzorno et al., "Novel Synthesis of 5,6,7,8–Tetrahydroindolizines", Journal of Organic Chemistry, vol. 42, No. 5, pp. 909–910, Mar. 1977.

Hassner et al., "Intramolecular Formation of Oxazolium Salts and Their Reaction With N– and C–Nucleophiles", Tetrahedron Letters, vol. 31, No. 25, pp. 7213–7214, 1990.

Pyl et al., Justus Liebigs Annalen der Chemie, 679, 1964, 139–144.

Molloy et al., Journal of the Chemical Society, 1965, 65–71.

Galera et al., Journal of Heterocyclic Chemistry, 23, 1986, 1889–1892.

Buchan et al., Journal of Organic Chemistry, 42(14), 1977, 2448–2454.

Meyers et al., Chemical Abstracts, 76(3), 1972, abstract No. 14391j.

Kibirev et al., Chemical Abstracts, 61(1), 1964, abstract No. 5629g.

Weuffen et al., Chemical Abstracts, 64(1), 1966, abstract No. 5488e.

Alekseeva, Chemical Abstracts, 84(17), 1976, abstract No. 120952t.

Druzhinina et al., Chemical Abstracts, 80(25), 1974, abstract No. 146165f.

Druzhinina et al., Chemical Abstracts, 68(11), 1968, abstract No. 49510j.

(List continued on next page.)

Primary Examiner—Mukund J. Shah
Assistant Examiner—Brenda Coleman
Attorney, Agent, or Firm—Bacon & Thomas

[57] ABSTRACT

The present invention relates to heterocyclic compounds of the formula

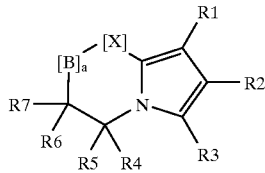

I in which $R^1-R^7$, B, a and X have the meanings recited in the specification. These compounds are usable in the treatment of diseases of the rheumatoid group and for the prevention of allergically induced diseases.

9 Claims, 9 Drawing Sheets

OTHER PUBLICATIONS

Ceder et al., *Chemical Abstracts*, 77(19), 1972, abstract No. 126481r.

Druzhinina et al., *Chemical Abstracts*, 77(13), 1972, abstract No. 88394e.

Alekseeva et al., *Chemical Abstracts*, 77(9), 1972, abstract No. 61153p.

Druzhinina et al., *Chemical Abstracts*, 86(17), 1977, abstract No. 121252t.

Brindley et al., *Chemical Abstracts*, 106(19), 1987, abstract No. 156332c.

Druzhinina et al., *Chemical Abstracts*, 87(1), 1977, abstract No. 5863q.

Derwent Abstract of EP 0 397 175, Dannhardt et al., 1998.

Dannhardt et al., *Archiv der Pharmazie*, 327(8), 1994, 509–514.

[A]-ANNELATED PYRROLE DERIVATIVES AND PHARMACEUTICAL USE THEREOF

This application is a 371 of PCT/EP95/02079 filed May 31, 1995.

The invention relates to pyrroles which are anellated at bond a, and their use in pharmacology, as well as to pharmaceuticals that contain these compounds.

It is known that arachidonic acid is metabolized by different routes. In the cyclooxygenase route, the arachidonic acid is metabolized into prostaglandins under the influence of the enzyme cyclooxygenase. In the lipoxygenase route, the arachidonic acid is metabolized into so-called leukotrienes under the influence of lipoxygenases.

The prostaglandins are involved in the development of inflammation, fever and pain, while the leukotrienes play an important role in the development of asthma, inflammations, and allergies. To fight these symptoms, nonsteroidal anti-inflammatory drugs are used, such as arylethanoic acid derivatives, 2-arylpropionic acid derivatives, and anthranilic acid derivatives. These derivatives inhibit the cyclooxygenase and thus prevent the formation of the prostaglandins from arachidonic acid. Such derivatives are not used without reservations with regard to their side effects, however. Drugs that inhibit lipoxygenase are not available on the market.

European Patent Disclosure EP-A-397 175 describes pyrrolizine compounds of the formula:

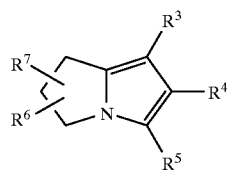

in which two of the radicals $R^3$, $R^4$ and $R^5$ independently of one another stand for H, $C_5$–$C_8$ cycloalkyl, $C_1$–$C_{12}$ alkyl or aryl, which is optionally substituted by one or two radicals, which are selected from the group comprising halogen, $NO_2$, $C_1$–$C_4$ alkoxy, $C_1$–$C_4$ alkyl or phenoxy, and the third of the radicals $R^3$, $R^4$ and $R^5$ stands for CHO, $CO_2H$, $COSC_1$–$C_4$ alkyl or A—X, where A stands for a straight-chain or branched $C_1$–$C_8$ alkylene group or a $C_2$–$C_8$ alkenylene group, and X stands for $CO_2H$, $SO_3H$, CHO, OH, or SH. These compounds are cyclooxygenase- and/or lipoxygenase-inhibitors, and are therefore usable in the treatment of diseases of the rheumatoid variety and for the prevention of allergically induced diseases.

Those compounds of the above formula in which A—X stands for $CH_2CO_2H$ are especially efficacious. However, they have a strong tendency to decarboxylate. For example, the half life in chloroform is ca. 1–2 h, while a 1% alkaline, aqueous solution decarboxylates at a rate of ca. 2% per day.

Surprisingly, it has now been found that certain heterocyclic compounds are chemically more stable, with a comparable effect. Moreover, the compounds also have novel effect qualities, such as lowering blood pressure, lipid reduction, and tracheal relaxation.

The subject of the invention is therefore heterocyclic compounds of formula I:

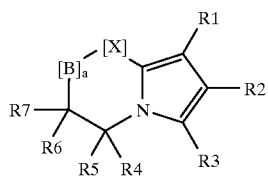

in which
two of the radicals $R^1$, $R^2$ and $R^3$, which may be identical or different, stand for a hydrogen atom, an aryl radical, which optionally has one or two substituents which are selected from the group comprising halogen, pseudohalogen, $CF_3$, $NO_2$, OH, alkoxy, $OCF_3$, alkyl and aryloxy, or a mono- or bicyclic aromatic heterocyclic radical which has at least one oxygen, nitrogen and/or sulfur atom and which is optionally condensed with a phenyl or napthyl radical and is optionally substituted by halogen, $CF_3$, alkyl or alkoxy, and
the third of the radicals $R^1$, $R^2$ and $R^3$ stands for $COCO_2H$, $COCO_2$ alkyl or A—Y,
A stands for $C_1$–$C_8$ alkylene or $C_2$–$C_8$ alkenylene,
Y stands for $CONR^8R^9$,
$R^8$ and $R^9$, which may be identical or different, stand for H, alkyl, OH, acyl, $SO_2$ alkyl, or $SO_2$ phenyl, and the alkyl radical of the sulfonyl group is optionally substituted by one or more halogen atoms and the aryl radical is optionally substituted by one or more halogen, $C_1$–$C_8$ alkyl, or $C_1$–$C_8$ alkoxy radicals,
$R^4$, $R^5$, $R^6$ and $R^7$, which may be identical or different, stand for H or alkyl, or two of the vicinal radicals stand for a chemical bond between the two ring atoms to which they are bonded and the other two have the meanings stated, or two of the geminal radicals together with the carbon atom to which they are bonded stand for a carbonyl group,
X stands for $CH_2$, CO, O, S, SO, $SO_2$, or $NR^{10}$, where $R^{10}$ stands for H, alkyl or aryl, which is optionally substituted by halogen, $C_1$–$C_8$ alkyl, or $C_1$–$C_8$ alkoxy,
B stands for $CH_2$ or $CH_2CH_2$,
a stands for 0, 1 or 2, and
their optical isomers, salts and esters.

Figure 1A:
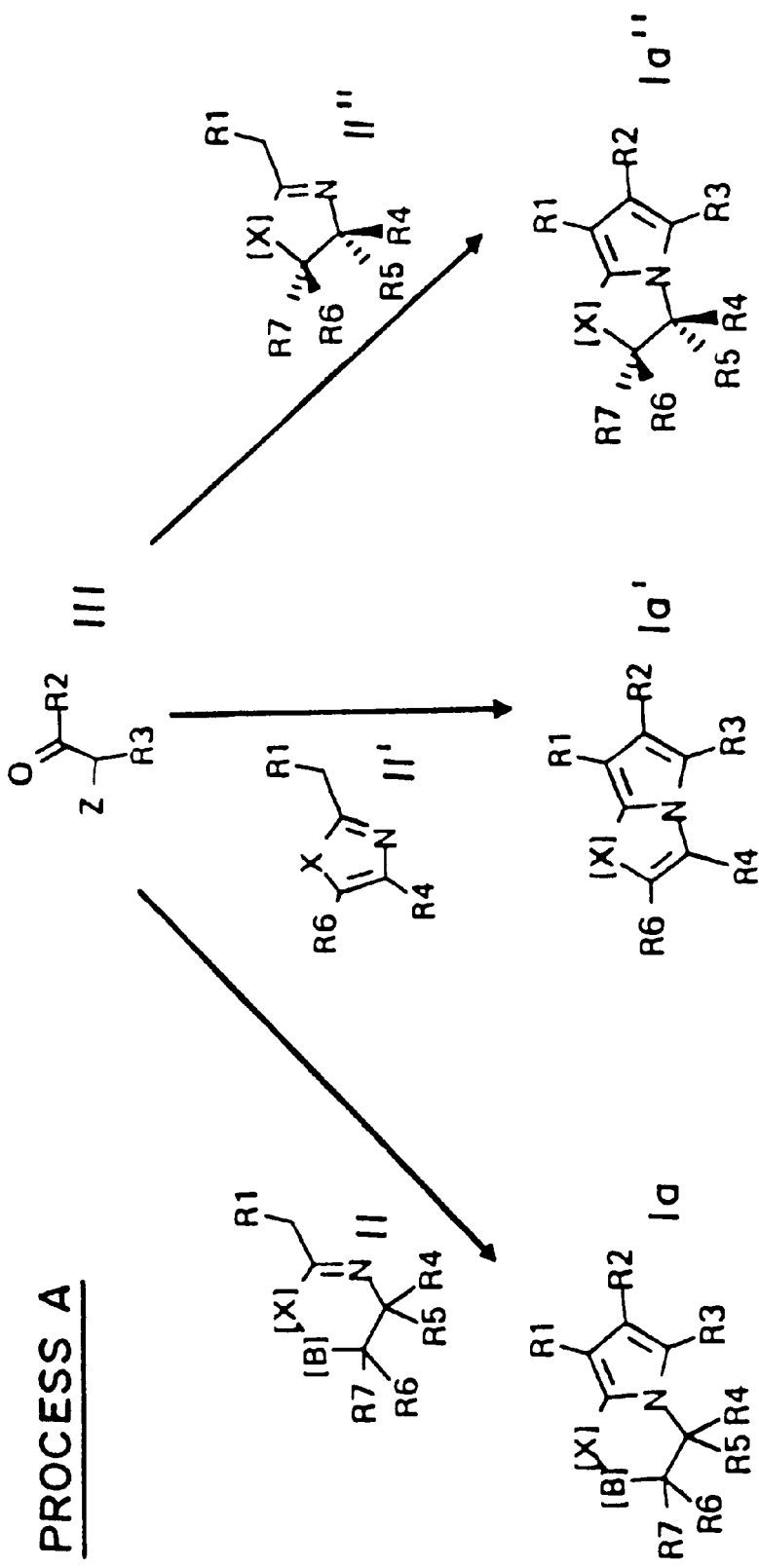
FIGS. 1a–1c, 2, 3a, 3b, 4, 5a and 5b are flow sheets depicting processes A to O which are chemical synthesis processes analogous to the processes used to make the compounds according to the invention.

The pharmaceutically compatible salts in the present case can be acid addition salts or base addition salts. Inorganic acids such as hydrochloric acid, sulfuric acid, or phosphoric acid, or organic acids such as tartaric acid, lactic acid, citric acid, malic acid, mandelic acid, ascorbic acid, maleic acid, fumaric acid, gluconic acid, and the like are used for acid addition salts.

Base addition salts include salts of the formula I compounds with inorganic bases such as sodium hydroxide or potassium hydroxide or with organic bases such as monoethanolamine, diethanolamine, or triethanolamine.

The esters of the formula I compounds, in particular include esters that are physiologically easy to hydrolyze, for example alkyl ester, pivaloyloxymethyl ester, acetoxymethyl ester, phthalidyl ester, indanyl ester, and methoxymethyl ester.

The term "alkyl, alkoxy, etc." includes straight-chain or branched alkyl groups such as methyl, ethyl, n-propyl and i-propyl, n-butyl, i-butyl, or t-butyl, n-pentyl, neopentyl, n-hexyl, etc.

Unless otherwise indicated, "alkyl" preferably stands for $C_1$–$C_8$ alkyl, in particular for $C_1$–$C_6$ alkyl, and in particular preferably, for $C_1$–$C_4$ alkyl.

"Aryl" preferably stands for naphthyl and in particular for phenyl.

The term "halogen atom" includes a fluorine, chlorine, bromine, or iodine atom and in particular for a fluorine or chlorine atom. "Pseudohalogen" particularly stands for CN, OCN, SCN, or $N_3$.

"Alkylene" or "alkenylene" stands for straight-chain or branched alkylene or alkenylene groups with preferably 1 to 6 or 2 to 6 and in particular 1 to 4 or 2 to 4 carbon atoms. The alkylene group and in particular the methylene group is preferable.

"Acyl" stands for RCO, where R preferably has the meanings stated for "alkyl" and "aryl". Acetyl is particularly preferable.

The "aromatic, heterocyclic radical" refers in particular to a 5- and 6-member heterocyclic radical that can be substituted and anellated as indicated above. Examples are a thiophene, pyrrole, imidazole, thiazole, thiadiazole, furan, oxazole, isoxazole, pyridine, pyrimidine, benzofuran, or quinoline radical. If the heterocycle is substituted, 1, 2, or 3 substituents are available, which are selected from the group comprising halogen, $CF_3$, $C_1$–$C_8$ alkyl, and $C_1$–$C_8$ alkoxy. A thiophene- or halogen-substituted, in particular chlorine-substituted, thiophene radical, or a furan, pyridine, benzofuran or quinoline radical is preferable.

If one of the radicals $R_1$, $R_2$, and $R_3$ means a heterocyclic radical or a substituted aryl radical, then $R_2$ preferably stands for such a radical.

The substituents of the aryl group are preferably selected from the group comprising halogen, in particular fluorine or chlorine, $CF_3$, $NO_2$, and phenoxy. If the aryl group is a phenyl ring, the substituents are preferably situated in the m-position and/or the p-position.

If Y stands for $CONR^8R^9$, then $R^8$ preferably stands for a hydrogen atom or an alkyl group and $R^9$ stands for optionally halogen- substituted $SO_2C_1$–$C_8$ alkyl or optionally $C_1$–$C_8$ alkyl- substituted $SO_2$ phenyl, in particular $SO_2CH_3$, $SO_2CF_3$, $SO_2$ phenyl or $SO_2$ tolyl.

Preferably the third of the radicals $R^1$, $R^2$, and $R^3$ is situated in the 5-position of the pyrrolizidine structure.

A preferred embodiment is the compounds of above formula I, in which two of the radicals $R^1$, $R^2$ and $R^3$, independently of one another, stand for H, phenyl, halogen- or $CF_3$-substituted phenyl (one, two or three halogen atoms), or for a 5- or 6-member heterocyclic ring of the above-defined type, and the third of the radicals $R^1$, $R^2$, and $R^3$ stands for A—Y, where A stands for $C_1$–$C_8$ alkylene and Y stands for $CONR^8R^9$, where $R^8$ and $R^9$ have the meanings indicated above.

Another preferred embodiment is the compounds of the above-mentioned formula I, in which $R^1$ stands for H or phenyl, $R^2$ stands for phenyl, halogen-substituted phenyl, or a 5- or 6-member heterocyclic ring, and $R^3$ stands for A—Y, where A and Y have the meanings stated.

In a particularly preferable manner, A—Y stands for $CH_2CONHSO_2R$, where R stands for $CH_3$, $CF_3$, phenyl, or tolyl.

X preferably stands for $CH_2$; B preferably stands for $CH_2$; a preferably stands for 0.

A particularly preferable set of embodiments is the compounds of the above-mentioned formula I, in which two of the radicals $R^4$ and $R^6$ or $R^5$ and $R^7$ together stand for a chemical bond or in which the radicals $R^4$–$R^7$ stand for H or alkyl. These compounds have the formula:

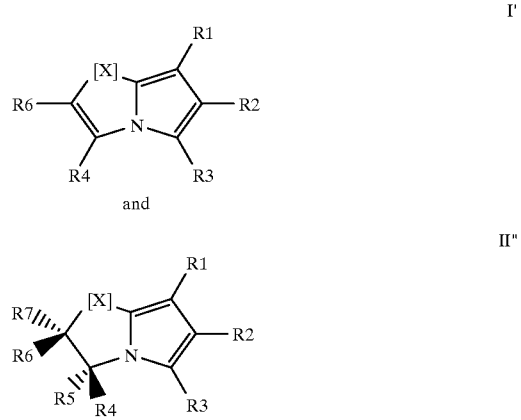

The radicals $R^1$ to $R^7$ and X have the meanings stated.

A further preferred embodiment is the compounds of formula I″, in which if X stands for $CH_2$, then $R^6$ and $R^7$ stand for alkyl and $R^4$ and $R^5$ stand for hydrogen, and if X stands for S, then $R^6$ and $R^7$ stand for H and $R^4$ and/or $R^5$ stand for alkyl.

If the compounds according to the invention have asymmetry centers, racemates as well as optical isomers (enantiomers, diastereomers) are included.

The synthesis of the compounds according to the invention takes place analogous to the processes A to O described in FIGS. 1a–c, 2, 3a, 3b, 4, 5a and 5b. These methods are partially described in European Patent Disclosure EP-A-397 157; reference is hereby made to this publication and the literature references mentioned therein.

Figure 1B:
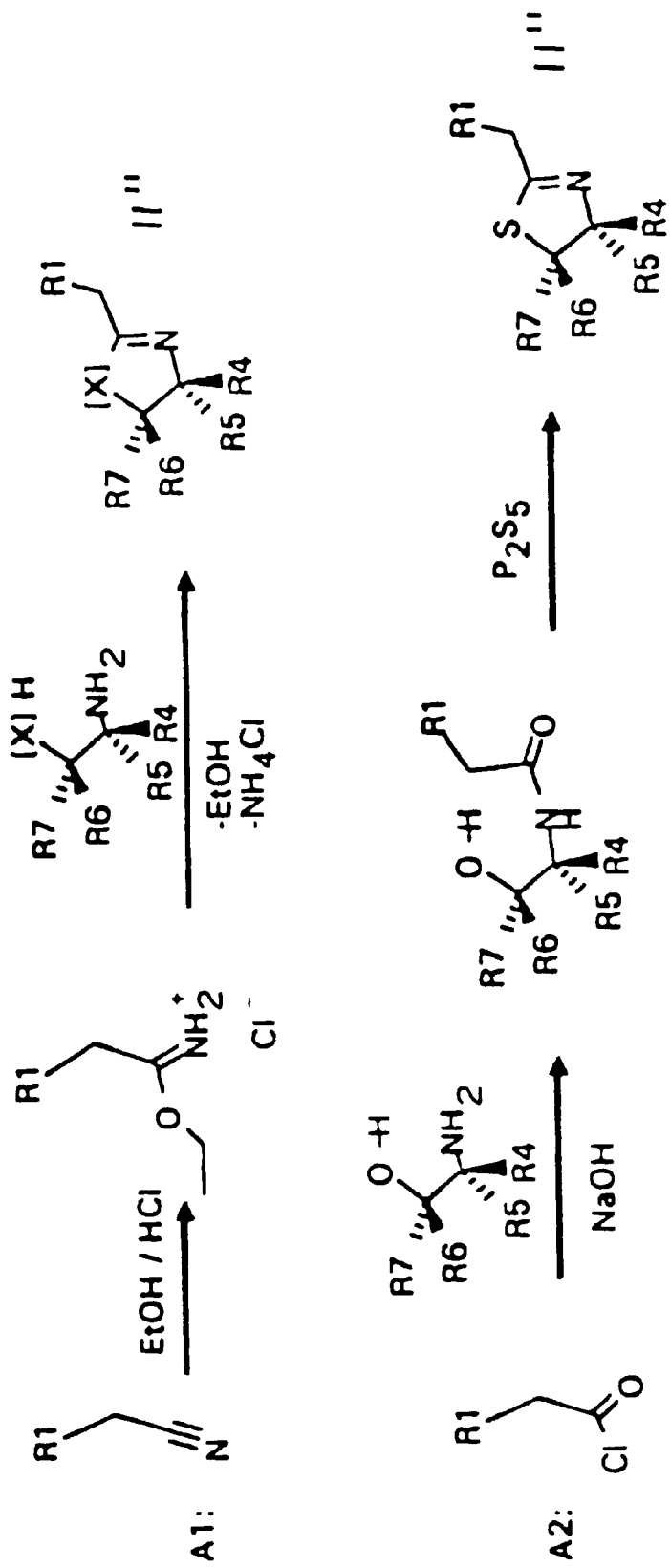
Figure 1C:
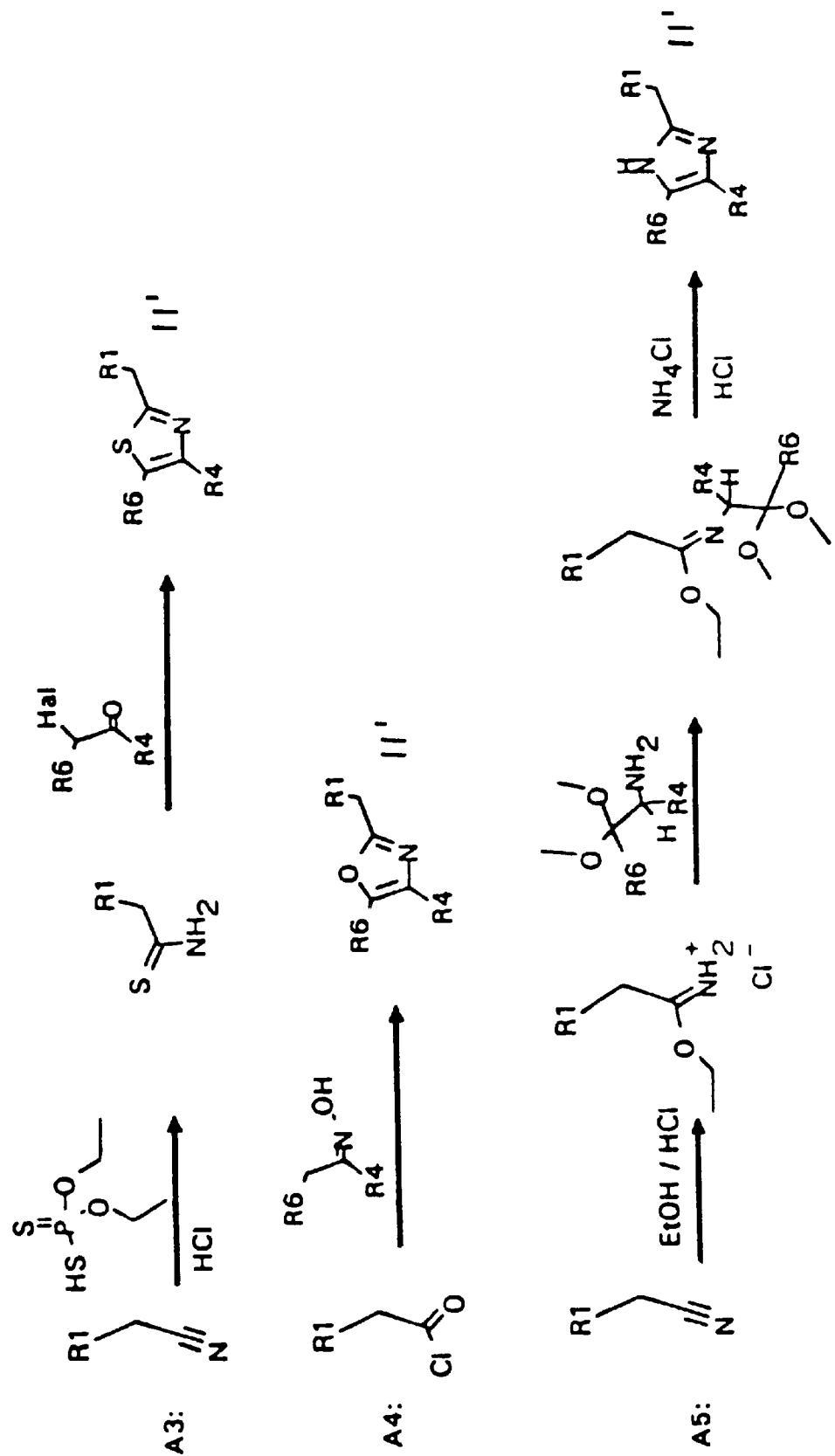

Initial compounds for the production of the compounds according to the invention are the compounds of formula II:

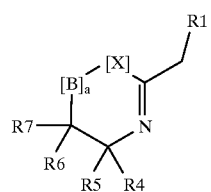

where $R^1$, $R^4$–$R^7$, and X have the meanings stated. These compounds are known in the literature, or they can be produced analogously to known processes, for example by those described in EP-A-397 175 (X=$CH_2$, CO) through the reaction of aminothiols, diamines, and amino alcohols derived from D- and L-amino acids with the imide esters of correspondingly substituted carboxylic acids (FIG. 1b A1/A2). The formula II compounds are reacted with the corresponding compounds of formula III.

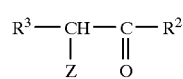

in which Z stands for Cl or Br and $R^2$ and $R^3$ have the desired meanings. The formula III compounds are likewise known from the literature or they can be produced analogously to known processes, for example those compounds in which $R^2$ stands for an aromatic, heterocyclic radical are produced analogous to the processes described by J. J. Riehl in C. R. Hebd. Seance. Acad. Sci. Ser. C (1957), 245, pp. 1321–1322. The reaction takes place an inert solvent (such as ethanol, methylene chloride, diethyl ether, tetrahydrofuran) in the presence of a suitable base (such as $NaHCO_3$, triethylamine). If X stands for 0, S or $NR^{10}$, the reaction takes place preferably in an ether or aromatic hydrocarbon, such as diethyl ether, benzene or toluene; the quaternized intermediate product precipitates out. This product is isolated and dissolved in a chlorinated solvent, such as $CH_2Cl_2$, and treated with a base, such as triethylamine.

This reaction produces the formula Ia compounds:

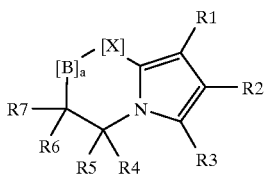

If at least one of the radicals $R^1$, $R^2$, and $R^3$ stands for a hydrogen atom, compounds of the following formulas IVa through IVc are obtained:

IVa
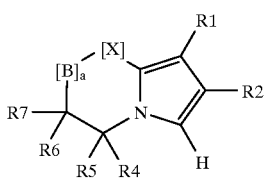

IVb
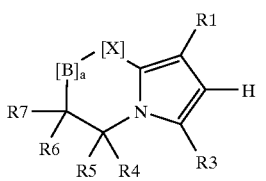

IVc
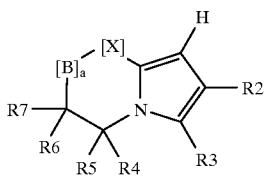

The compounds of series a, b, or c are derived from this depending on the position of the hydrogen atom.

This reaction as well as the reactions mentioned below are outlined in FIGS. 1a–c, 2, 3a, 3b, 4, 5a, and 5b in the example of the compounds of series a. The same is true for the synthesis and derivative production of the compounds of series b and c.

In addition to the process described in European Patent Disclosure EP-A-397 175 (process A), another process (process B) is used for the composition of heterocycles IVa, IVb, and IVc, where X=O, S or $NR^{10}$ (FIG. 2): the starting point of this process is correspondingly substituted 2-(5H) furanones (VI), which are produced from carboxylic acid salts of structure V and the halogen aldehydes and halogen ketones of structure III (FIG. 2), analogous to the methods described in the literature (a: Rio, G. and Sekiz, B. Bull. Soc. Chim. Fr. 1976, 1491, 1495. b: Padwa, A., Brookhart, T., Dehm, D., and Wubbels, G., J. Am. Chem. Soc. 1978, 100, 8247, 8259). Analogous to methods known from the literature, these are transformed into 1,5-dihydro-2-pyrrolones (VII or VIII) (c: Matsuda et al. Yakugaku Zasshi 95, [1975] 190, 194 (C.A. 83 [1975] 42 780; d: Rio, G. and Sekiz, B., see above).

Figure 2:
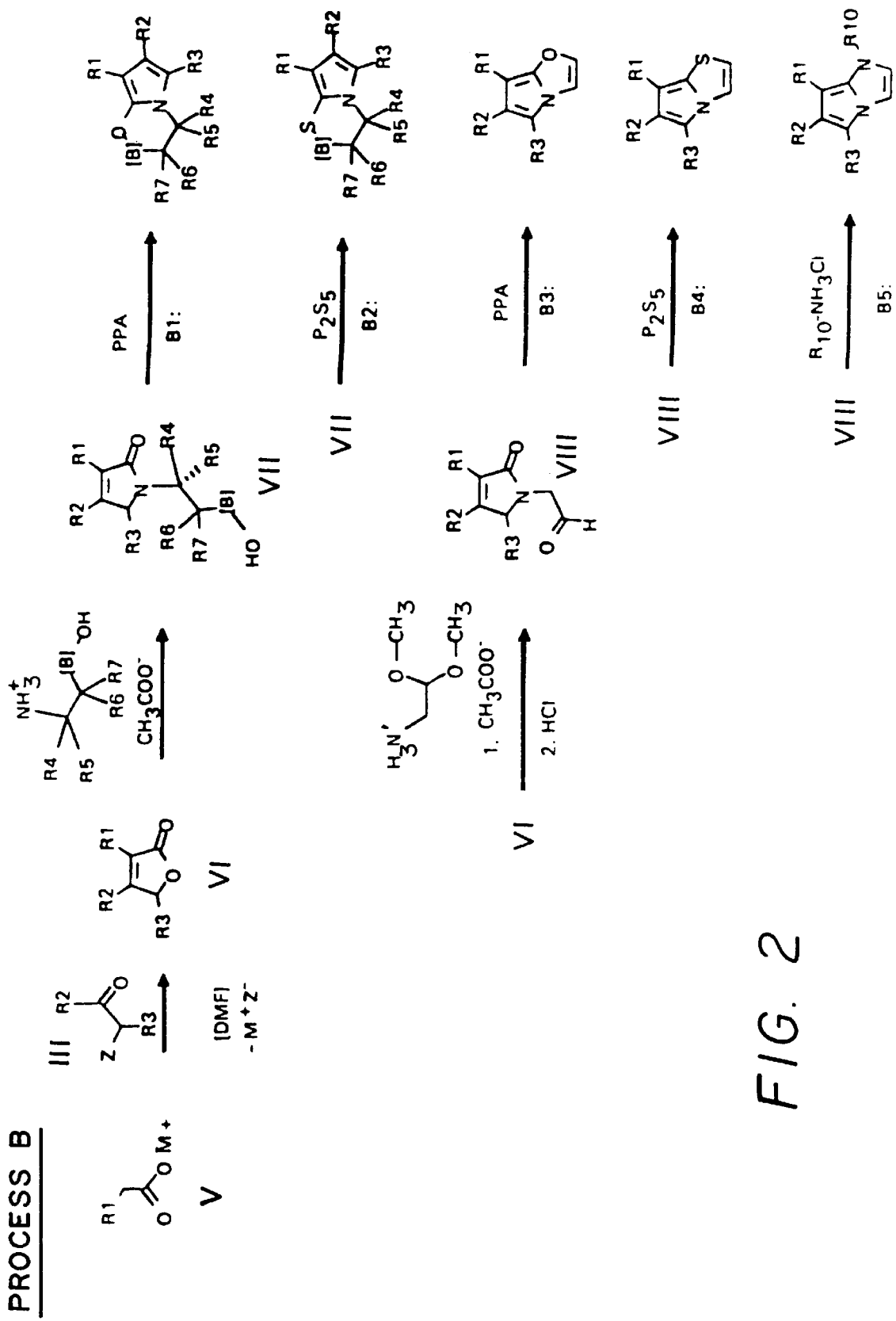

Depending on the condensation reagent used and on the second functional group of the bifunctional amines $NH_2$—$CR^4R^5CR^6R^7$—$[B]_a$—OH or $NH_2CH_2CH(OCH_3)_2$, the cyclization to the anellated heterocycle leads to partially hydrated forms (formula I'', FIG. 2: B1/B2) or to dehydrated forms (formula I', FIG. 2: B3, B4, B5).

Figure 3A:
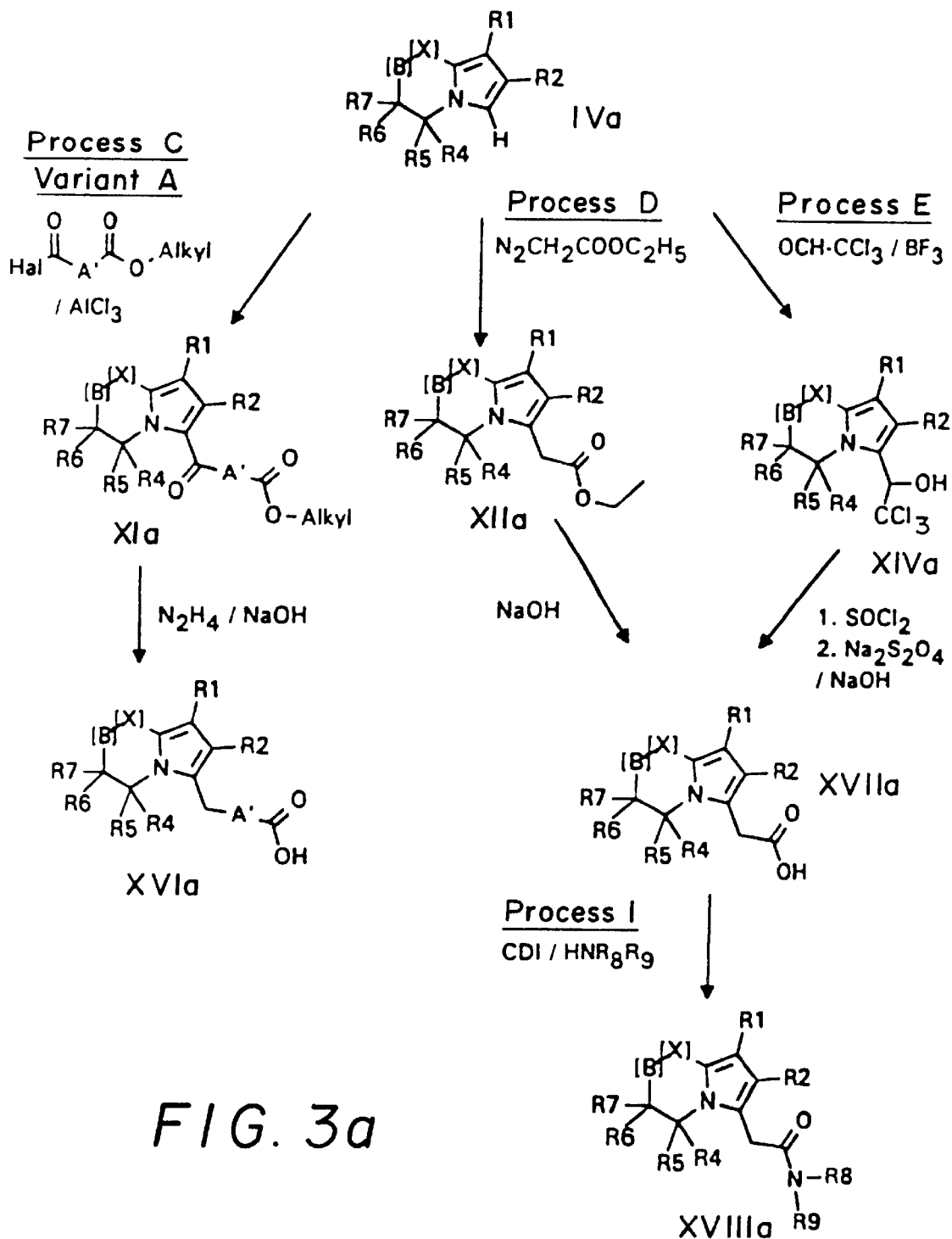
Figure 3B:
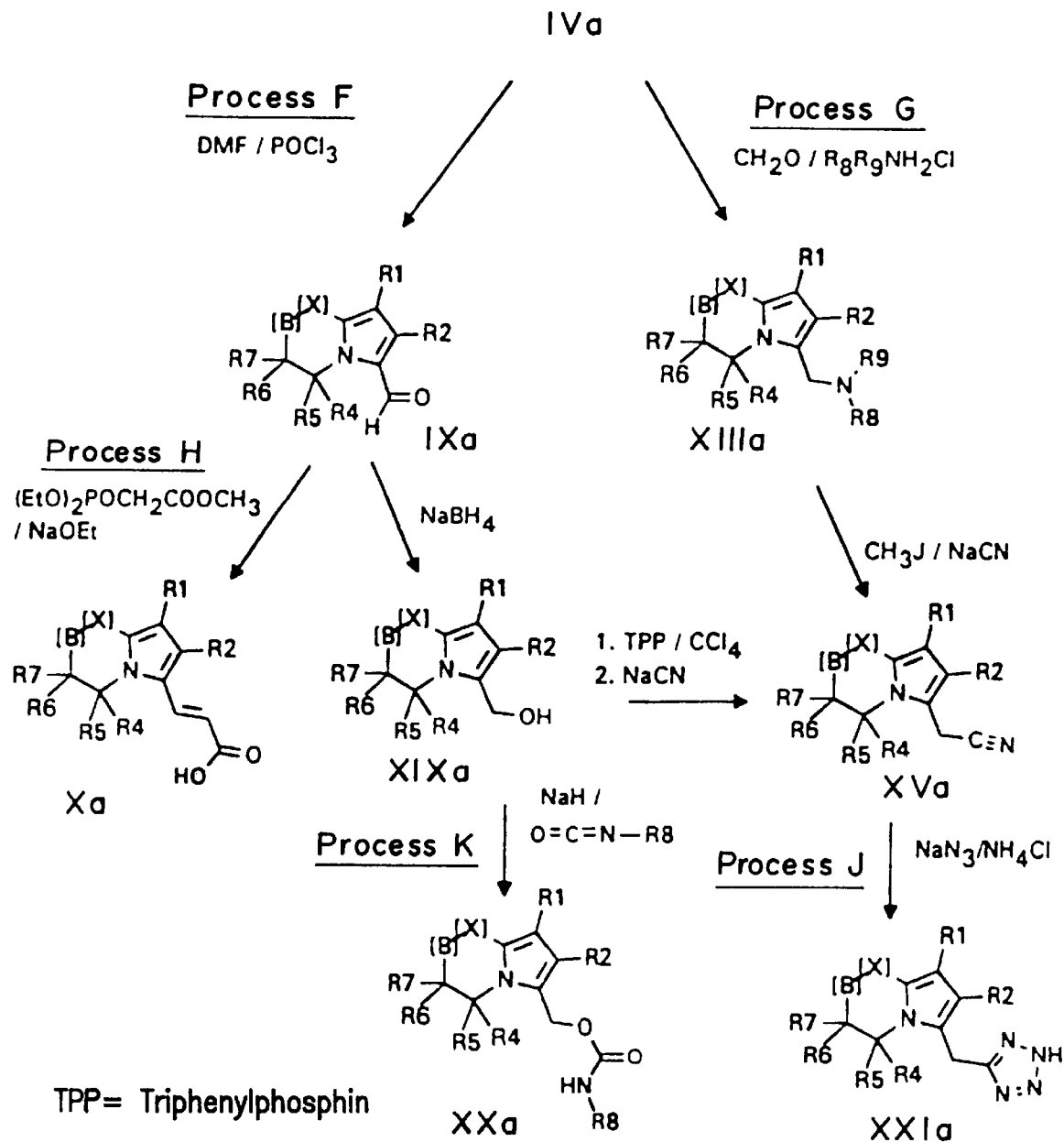
Figure 4:
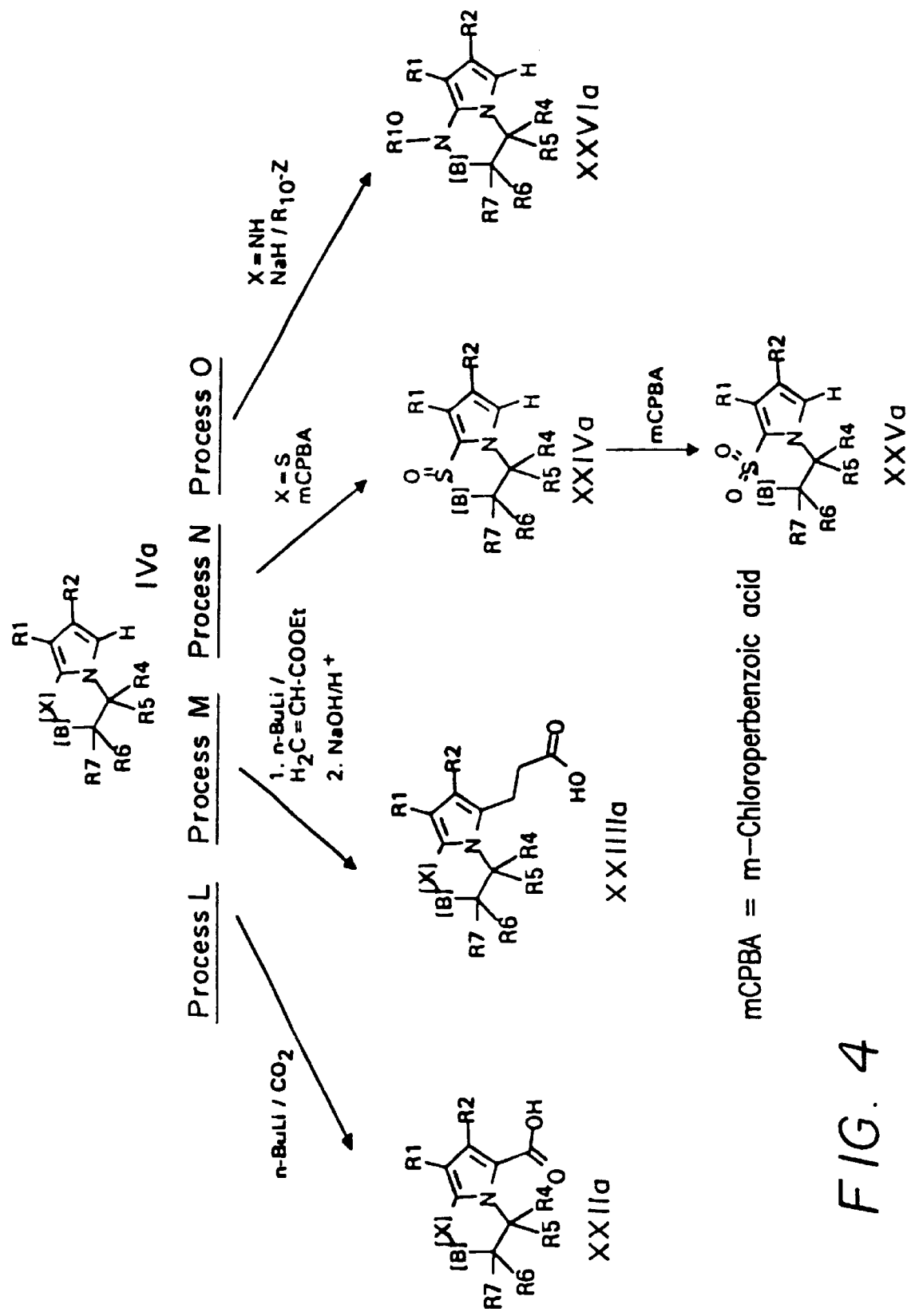
Figure 5A:
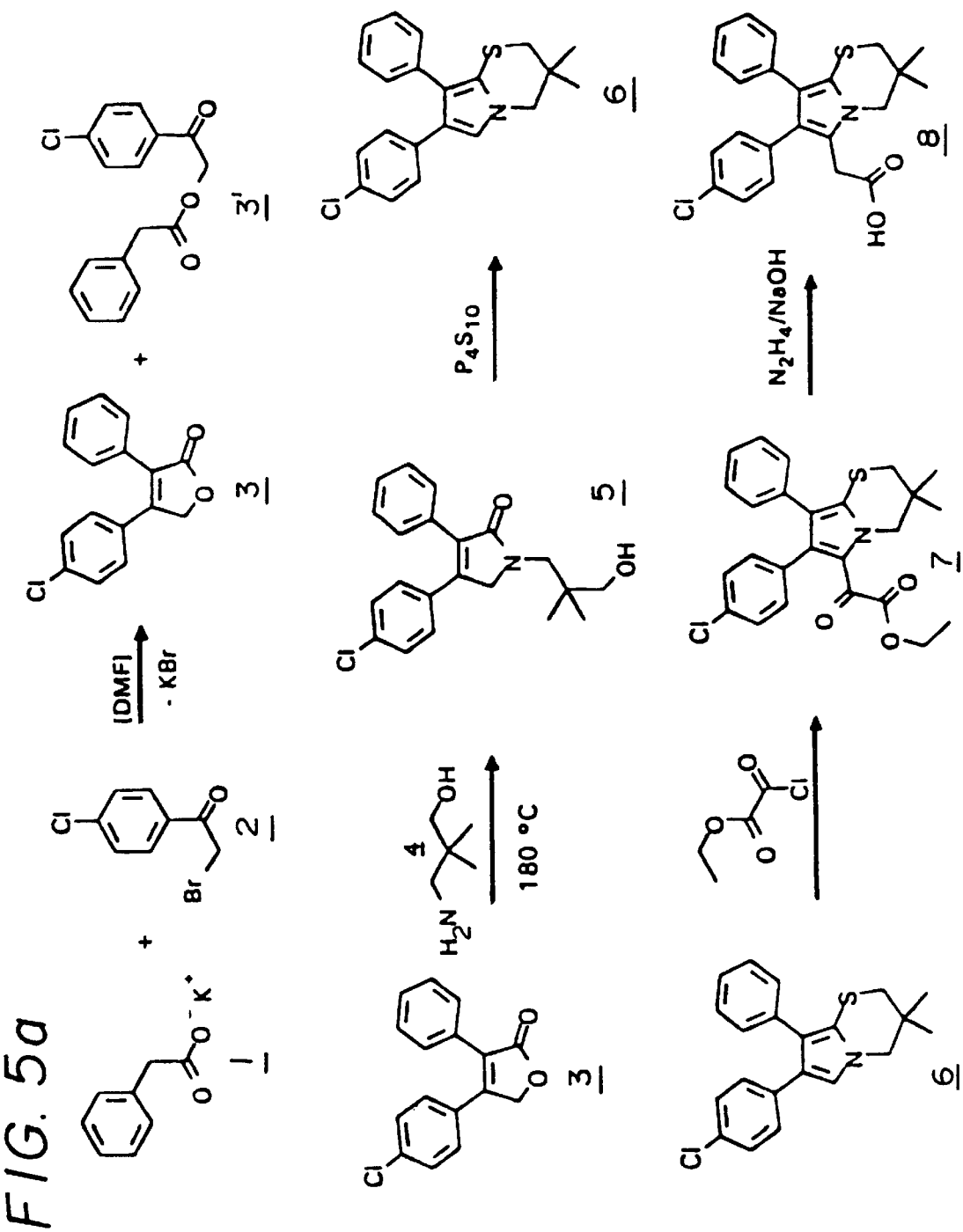
Figure 5B:
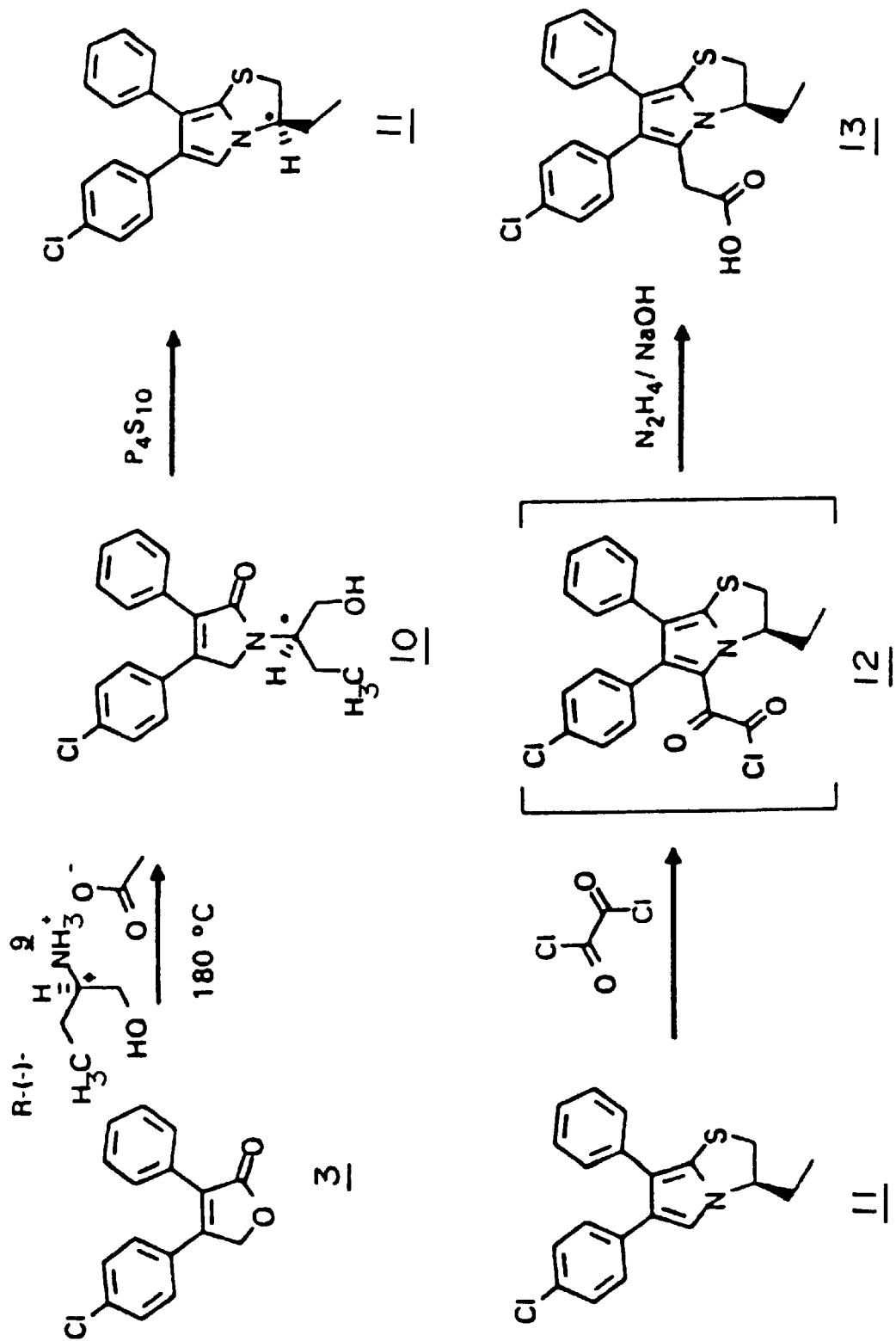

To insert the substituent A—$CONR^8R^9$, the radical A—$CO_2H$ is first inserted, by methods known to one skilled in the art. These methods include, for example:

a) Reaction of a formula Ia compound with a carboxylic acid halogenide HalOC—A'—COO alkyl, in which A' stands for a chemical bond, $C_1$-$C_7$ alkylene or $C_2$-$C_7$ alkenylene and Hal stands for Cl or Br (FIG. 3a, process C/variant A). The formula Ia compound obtained, in which one of the radicals $R^1$, $R^2$, and $R^3$ stands for CO—A'—$CO_2$ alkyl, is then treated with a reagent which is suitable for the reduction of the carbonyl group to a $CH_2$ group, for example hydrazine, $NaCNBH_3$ or zinc amalgam. The reaction with the carboxylic acid halogenide is carried out in an inert solvent, e.g. diethyl ether or tetrahydrofuran, optionally in the presence of a catalyst. The reduction with hydrazine under the conditions of a Wolff-Kishner reduction, and especially the Huang-Minlon Variant of it, is preferred. The reduction with hydrazine is preferably carried out in a high-boiling alcohol, e.g. diethylene glycol. The formula XVI compound is obtained in this manner.

b) There are a number of methods available for inserting the particularly preferable group $CH_2CO_2H$ (see FIGS. 3a, 3b, and 4). The first possibility comprises reacting a formula IV compound with oxalyl chloride (FIG. 5b), wherein a formula I compound is obtained, in which one of the radicals $R^1$, $R^2$, and $R^3$ stands for $COCO_2H$. This compound is then treated with a reagent which is suited to the reduction of the ketocarbonyl group, for example hydrazine, $HaCNBH_3$, or zinc amalgam (also see point a) above).

Another possibility comprises reacting a formula IVa compound with a diazoethanoic acid alkyl ester producing a formula I compound in which one of the radicals $R^1$, $R^2$, and $R^3$ stands for $CH_2COO$ alkyl. If so desired, this compound is then subjected to ester cleavage into the corresponding free carboxylic acid. (FIG. 3a, XVII).

The reaction with the diazoethanoic acid is carried out in an inert solvent, for example toluene or xylene, in the presence of copper powder or complex copper(I) salts or copper(II) salts. The reaction is carried out at an increased temperature, suitably at the boiling temperature of the solvent used.

A further possibility comprises the reaction of a formula IV compound with chloral producing a formula XIV compound and treatment of the activated compound with a dithionite, for example sodium dithionite or rongalite (hydroxymethane sulfinic acid sodium salt); see FIG. 3, process E.

c) The insertion of a formyl group group into the pyrrole ring is carried out through the reaction of a formula IV compound with phosphorus oxychloride/dimethyl formamide (see FIG. 3b). The reaction is carried out in an inert solvent, for example benzene, toluene, or xylene, at an increased temperature, suitably at the boiling point of the solvent used. A formula IX compound is obtained, in which one of the radicals $R^1$, $R^2$, and $R^3$ stands for CHO. The —CHO group can then be reduced in a usual way, for example with $LiAlH_4$, in an inert solvent, for example tetrahydrofuran, forming the corresponding hydroxymethyl compound XIX (FIG. 3b). This can then be used for further reactions for the insertion of the desired groups (process K, J; FIG. 3b).

The formyl group in a Wittig reaction carried out under normal conditions can be transformed into a corresponding alkenylene group producing the compound X (see compound X in FIG. 3b). If so desired, this can in turn be hydrated in a usual way, forming the corresponding alkylene compound (XXIII, FIG. 4).

d) Reaction of a formula IV compound with an anhydride with the formula:

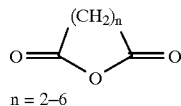

n = 2–6 produces the corresponding formula I ketocarboxylic acids, in which one of the radicals $R^1$, $R^2$, and $R^3$ stands for $CO(CH_2)_nCO_2H$. With the reagent already mentioned, the ketocarbonyl group can be reduced to a $CH_2$ group (see FIGS. 3, 3a, XI–XVI).

The preparation of the formula I compounds, in which one of the radicals $R^1$, $R^2$, and $R^3$ stands for $A—CONR^8R^9$, is then done starting with the corresponding activated derivative of carboxylic acid of formula Ia, in which one of the radicals $R^1$, $R^2$, and $R^3$ stands for $ACO_2H$, by reaction with the corresponding sulfonamide, amine, amide or hydroxylamine (see FIG. 2). Suitable activated carboxylic acid derivatives are known to one skilled in the art; the imidazole derivative is preferred.

The reaction is performed in an inert solvent, for example an ether, such as diethyl ether or tetrahydrofuran, in the presence of a base, such as sodium hydride. The reaction temperature is in the range from room temperature to the boiling point of the solvent. Expediently, the reaction is performed at room temperature.

The compounds according to the invention have proved to be potent cyclooxygenase and/or lipoxygenase inhibitors. They can therefore be used in the treatment of diseases which are associated with a change in arachidonic acid metabolism. In particular, this pertains to diseases of the rheumatoid variety and the prevention of allergically induced diseases. The compounds according to the invention consequently represent effective anti-inflammatory drugs, analgesics, antipyretics, antiallergics, and broncholytics or are effective against bronchial constriction and can therefore be used for thrombosis prophylaxis and for the prophylaxis of anaphylactic shock as well as for the treatment of dermatological diseases such as psoriasis, urticaria, acute and chronic exanthemas of allergic and non-allergic genesis. They are also usable for treating lipid exchange, in particular in order to lower cholesterol.

The compounds according to the invention, as compared with the corresponding carboxylic acids, have considerably greater stability in solution. Thus 6-(4-chlorophenyl)-2,2-dimethyl-7-phenyl-2,3-dihydro-1H-pyrrolizin-5-yl acetic acid in chloroform, with a half life of ca. 1 h and in aqueous solution (sodium salt) decarboxylates at a rate of ca. 2% per day. The analogous methane sulfonamide, conversely, is stable, with a largely unchanged profile of efficacy.

The compounds according to the invention can be administered either as individual therapeutic agents or as mixtures with other therapeutic agents: They can be administered as is, but in general, they are administered in the form of pharmaceuticals, that is, as mixtures of agents with suitable pharmaceutical vehicles or diluents. The compounds or agents can be administered orally or parenterally, preferably, though, they are given in oral dosage forms.

The type of pharmaceutical and the type of pharmaceutical vehicle or diluent depend on the desired type of administration. Oral agents can be in tablet or capsule form and can contain conventional excipients such as binders (e.g. syrup, acacia, gelatine, sorbitol, tragacanth, or polyvinyl pyrrolidone), fillers (e.g. lactose, sugar, cornstarch, calcium phosphate, sorbitol, or glycine), lubricants (e.g. magnesium stearate, talcum, polyethylene glycol, or silicon dioxide), disintegrating agents (e.g. starch), or wetting agents (e.g. sodium lauryl sulfate). Oral fluid preparations can be in the form of aqueous or oleaginous suspensions, solutions, emulsions, syrups, elixirs, or sprays, etc. or can be in the form of dry powder for reconstitution in water or another suitable vehicle.

Fluid preparations of this kind can contain conventional additives, for example suspension agents, flavorings, diluents, or emulsifying agents. For parenteral administration, solutions or suspensions can be used with standard pharmaceutical vehicles.

The compounds or agents according to the invention can be administered to a mammal (human and animal) in doses of approximately 0.5 mg to approximately 100 mg per kg of body weight per day. They can be administered in a single dose or in a number of doses.

The spectrum of efficacy of the compounds was investigated using the following tests:

1) Phenylquinone writhing test in the mouse p.o., S. Irwin, Psychopharmacologia, 13:222–257, 1968;
2) Formalin analgesia test in the mouse p.o., B. Rubin et al., Endocrinol., 49:429–439, 1951;
3) Inhibition of arachidonic acid-induced platelet aggregation, V. Bertele et al., Science 220:517–519 (1983);
4) Inhibiting inflammation in rat paw edema, C. A. Winter et al., Proc. Exper. Biol. Med., 111:544–547 (1962);
5) Tracheal relaxation in the guinea pig, F. P. Luduena et al., Arch. Int. Pharmacodyn., 111:392–400, 1957;
6) Cholesterol-reducing action in the mouse, C. E. Day et al., Atherosclerosis Drug Discovery, Ed. Charles E. Day, Plenum Publishing Corp., New York, 1976, 231–249.
7) $IC_{50}/LO/CO$: Inhibition of the enzyme cyclooxygenase (CO) and 5-lipoxygenase (LO), Dannhardt et al., J. Pharm. Pharmacol. 1992, 44:419–424.

The results are given in the following Table 1:

| Comp.[1/] | 1 | 2 | 3 | 4 | 5 | 6 | 7 |
|---|---|---|---|---|---|---|---|
| 3 | x | x | x | - | x | x | - |
| 4 | x | - | x | x | x | - | $2,3/1,5 \times 10^{-7}$ |
| 5 | - | - | x | - | - | x | - |
| 6 | - | - | x | - | - | - | - |
| 7 | - | - | x | x | x | - | - |
| 8 | - | - | x | - | - | x | - |
| 9 | x | x | x | x | - | - | - |
| 10 | x | - | x | - | - | x | - |
| 11 | x | - | x | - | - | - | - |
| 12 | - | x | x | - | - | x | - |
| 13 | - | - | - | - | x | x | - |

The following examples explain the invention. All temperature data is uncorrected. The IR spectra, unless otherwise indicated, were picked up from KBr compacts. Unless otherwise noted, the NMR spectra are 200 MHz spectra, picked up in CDCl₃ with tetramethylsilane (TMS) as an internal standard. The IR spectra are indicated in cm⁻¹ and the NMR spectra are indicated in δ(ppm).

EXAMPLES

General recipe for preparing aryl-substituted [a]- or [1,2]-anellated pyrroles (pyrrolo[1,2-a]pyrroles=pyrrolizines, pyrrolo[1,2-a]pyridines=indolizines, pyrrolo[1,2-a]azepines)

To a solution of 20 mmol omega-bromacetyl compounds in 100 ml methylene chloride, 20 mmol of the corresponding cyclic imine derivative in 50 ml of methylene chloride is added quickly drop by drop and stirred for 4 h at room temperature with the exclusion of moisture. Next, 30 ml of 5% aqueous NaHCO₃ solution is added, and the mixture is stirred intensively for another 4 h. After the addition of 200 ml of water, the organic phase is separated off, dried over Na₂SO₄, and evaporated at reduced pressure. The residue is made to crystallize with methanol, and optionally recrystallized from methanol.

General Recipe for Preparing Aryl-Substituted [a]- or [1,2]-Anellated Pyrrol-5-yl-Oxoacetic Acids To a solution of 1.4 mmol oxalic acid ethyl ester chloride in 20 ml of dry methylene chloride, 1.3 mmol of correspondingly substituted anellated pyrrole, dissolved in 20 ml of dry methylene chloride, is added drop by drop while stirring, and stirring is continued for 20 min. After 40 ml of water is carefully added, the organic phase is separated out and dried over Na₂SO₄. The residue remaining after the solvent has been extracted is suspended in 20 ml diisopropyl ether aspirated off, and rewashed two more times with 5 ml of diisopropyl ether each time.

General Recipe for Preparing Aryl-Substituted [a]- or [1,2]-Anellated Pyrrol-5-yl-Acetic Acids 2 mmol of the corresponding oxoester derivative are mixed with 2 ml of diethylene glycol and 1.5 ml of 80% hydrazine derivative and stirred for 30 min at 60° C. Next, 2.1 g of potassium hydroxide are added, and the reaction mixture is heated while stirring for 2 h to 140° C.

The still-warm mixture is added to 20 ml of ice water and adjusted with dilute phosphoric acid to pH=3–4; the raw product settled out as a solid. This is aspirated, rewashed several times with water, dried in a vacuum, and then washed several times with a little diisopropyl ether.

General Recipe for Preparing N-sulfonylated [a]- or [1,2]-Anellated Arylpyrrolcarboxylic Acid Amides Mixture A:

2.6 mmol of the applicable pyrrolcarboxylic acid are stirred with 5 mmol of carbonyl diimidazole in 25 ml dry tetrahydrofuran for 1 h at room temperature.

Mixture B:

3 mmol of the correspondingly substituted sulfonamide are dissolved in 20 ml dry tetrahydrofuran in an argon atmosphere, mixed with 3.3 mmol sodium hydride (mineral oil suspension), and stirred for 1 h at room temperature.

Mixture B is added in an argon atmosphere to mixture A and stirred for 40 h. The suspension is poured onto 40 ml of ice water, adjusted with dilute phosphoric acid to pH=4, and extracted multiple times with diethyl ether. After drying of the organic phase over Na₂SO₄ and extraction of the solvent, the remaining residue is recrystalized from isopropanol.

The intermediate compounds and final compounds obtained, along with their physical data, are given in the following Tables 2–5. The intermediate compounds for Examples 1, 2 and 13 are described in EP-A 397 175, and those for Examples 3–6, 9 and 10 are prepared analogously.

TABLE 2

Reference Examples

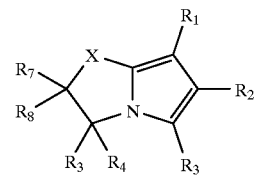

| Reference Example | X | R¹ | R² | R³ | R⁴ | R⁵ | R⁶ | R⁷ | X |
|---|---|---|---|---|---|---|---|---|---|
| 1 | | Ph | 5-Cl-2-thienyl | H | H | H | CH₃ | CH₃ | CH₂ |
| 2 | | Ph | 5-Cl-2-thienyl | COCO₂Et | H | H | CH₃ | CH₃ | CH₂ |
| 3 | | Ph | 5-Cl-2-thienyl | H | H | H | CH₂CH₃ | CH₂CH₃ | CH₂ |
| 4 | | Ph | 5-Cl-2-thienyl | COCO₂Et | H | H | CH₂CH₃ | CH₂CH₃ | CH₂ |
| 5 | | Ph | CO(CH₂)₃CO₂H | 5-Cl-2-thienyl | H | H | H | H | CH₂ |
| 6¹⁾ | | Ph | 5-Cl-2-thienyl | H | CH₃ | — | H | — | S |
| 7¹ | | Ph | 5-Cl-2-thienyl | CH₂CO₂Et | CH₃ | — | H | — | S |
| 8 | | Ph | 4-CF₃-phenyl | H | H | H | CH₃ | CH₃ | CH₂ |
| 9 | | Ph | 4-CF₃-phenyl | CH₂CO₂H | H | H | CH₃ | CH₃ | CH₂ |

¹⁾Compound of Formula 1'

TABLE 3

| Compound of Reference Example # | |
|---|---|
| 1 | B.P.: Oil<br>IR: 2950, 1656, 1596, 1444, 1414, 1382, 792, 759, 697<br>NMR: 7,29–7,17(m, 5H,arom); 6,71(s,1H,N—CH—);<br>6,70 (AB, J = 3,5, =CH—); 6,49 (AB,J = 3,5. =CH—); 3,72(s,2H,—CH₂—N); 2,75(s,2H, —CH₂—); 1,27(s,6H,—CH₃) |
| 2 | B.P. 133.0 C<br>IR; 2955, 1736, 1619, 1467, 1426, 1373, 1241, 1179, 1049, 701<br>NMR; 7,26–7,10(m, 5H, arom); 6,82 (AB, J = 3,7, |

TABLE 3-continued

| Compound of Reference Example # | |
|---|---|
| | —CH=); 6,77 (AB, J = 3,7, —CH=); 4,22 (s,2H, —CH₂N—); 3,87(q, 2H, J = 7,0, ethyl); 2,82(s,2H, —CH₂—); 7,31 (s,6H,—CH₂); 1,19(t,3H,J = 7,0, ethyl) |
| 3 | B.P. 80.3 C<br>IR; 2995, 1550, 1447, 1380, 1157, 1062, 986, 786, 758, 694<br>NMR; 7,30–7,15(m,5H,arom); 6,68(d,AB,1H,J = 4,0, thienyl); 6,47 (d,AB,1H, thienyl) (6,67(s,1H,—N—CH=); 3,74(s,2H,—CH₂—N); 2,73(s,2H, —CH₂pyr); |
| 4 | B.P. 126.8<br>IR; C=O; 1750, 1629<br>NMR; 7,31–7,09 (m, 5H, arom); 6,81 + 6,76(AB,2H,J = 3,7, —CH=CH—) 4,23(s,2H,—CH₂—N—); 3,87(q, 2H,J = 7,2, ethylester); 2,79 (s,2H,CH₂) |
| 5 | B.P. 126° C.<br>IR; 1660, 1706, (C=O)<br>NMR; 8,7–8,5(2H, Ar); 8,5–8,35(3H;Ar); 6,82(H_A, J_{AB} = 3,76Hz); 6,76 (H_B, J_{AB} = 3,75 Hz); 5,08 (t,2H, CH₂); 4,14(t,2H, CH₂); 3,67(quint.. 2H, CH₂); 3,53(t,2H, CH₂); 3,33 (t,2H, CH₂); 2,95 (quint.. 2H, CH₂). |

TABLE 3-continued

| Compound of Reference Example # | |
|---|---|
| 6 | NMR; 7,24–7,06 (m, 5H, Ar); 7,16 (s, 1H); 6,80, 6,62 (AB, J = 3,8 Hz, Thiophen-H); 6,31 (9,1H, J = 0.8 Hz); 2,40 (d, 3H, J = 0.8 Hz) |
| 7 | NMR; 7,26–7,03 (m, 5H, Ar); 6,80, 6,62 (AB, J = 3,8 Hz, Thiophen-H); 6,30 (9, 1H, J = 0,8 Hz); 3,51 (s, 2H, CH₂); 2,62 9,2H,6,8 Hz); 2,38 (d, 3H, 0,8 Hz); 1,12 (t, 3H, J = 6,8 Hz) |
| 8 | B.P. 104–105° C.<br>JR; 3435, 2960, 1608, 1315, 1158, 1121, 843, 762, 698<br>NMR; 7,48–7,15 (m, 9H, Ar); 6,75 (s, 1H); 3,75 (s, 2H, CH₂—N); 2,79(s, 2H, —CH₂—); 1,28 (s,6H, CH₃) |
| 9 | B.P. 174–174.5° C.<br>IR; 3420, 2960, 1706, 1319, 1156, 1110, 846, 758, 695<br>NMR; 7,5–7,04 (m, 9H, Ar); 3,77 (s, 2H, CH₂CO₂H); 3,6 (s, 2H, CH₂—N); 2,86 (s, 2H, —CH₂); 1,30 (s, 6H, CH₃) |

TABLE 4

EXAMPLES

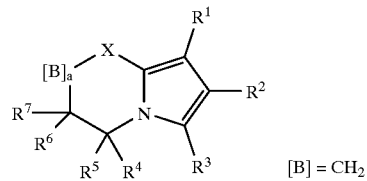

[B] = CH₂

| Nr. | R¹ | R² | R³ | R⁴ | R⁵ | R⁶ | R⁷ | X | a |
|---|---|---|---|---|---|---|---|---|---|
| 1 | Ph | Ph | CH₂—CONHOH | H | H | CH₃ | CH₃ | CH₂ | 0 |
| 2 | Ph | Ph | CH₂—CON(CH₃)OH | H | H | CH₃ | CH₃ | CH₂ | 0 |
| 3 | Ph | 4-Cl-ph | CH₂—CONHSO₂CF₃ | H | H | CH₃ | CH₃ | CH₂ | 0 |
| 4 | Ph | 4-Cl-ph | CH₂—CONHSO₂CH₃ | H | H | CH₃ | CH₃ | CH₂ | 0 |
| 5 | Ph | 4-Cl-ph | CH₂—CONHSO₂Ph | H | H | CH₃ | CH₃ | CH₂ | 0 |
| 6 | Ph | 4-Cl-ph | CH₂—CONHTosyl | H | H | CH₃ | CH₃ | CH₂ | 0 |
| 7 | Ph | 5-Cl-2-thienyl | CH₂—CONHSO₂CH₃ | H | H | CH₃ | CH₃ | CH₂ | 0 |
| 8 | Ph | 5-Cl-2-thienyl | CH₂—CONHTosyl | H | H | CH₃ | CH₃ | CH₂ | 0 |
| 9 | Ph | 4-Cl-ph | CH₂—CONHSO₂CH₃ | H | H | CH₂CH₃ | CH₂CH₃ | CH₂ | 0 |
| 10 | Ph | 4-Cl-ph | CH₂—CONHTosyl | H | H | CH₂CH₃ | CH₂CH₃ | CH₂ | 0 |
| 11 | Ph | 5-Cl-2-thienyl | CH₂—CONHSO₂CH₃ | H | H | CH₂CH₃ | CH₂CH₃ | CH₂ | 0 |
| 12 | Ph | 5-Cl-2-thienyl | CH₂—CONHTosyl | H | H | CH₂CH₃ | CH₂CH₃ | CH₂ | 0 |
| 13 | Ph | (CH₂)₄CONHTosyl | Ph | H | H | CH₃ | CH₃ | CH₂ | 0 |
| 14 | Ph | 5-Cl-thienyl | CH₂—CONHSO₂CH₃ | CH₃ | — | H | — | S | 0 |
| 15 | Ph | 4-CF₃—Ph | CH₂—CONHSO₂CH₃ | H | H | CH₃ | CH₃ | CH₂ | 0 |

TABLE 5

| Compound of Example # | |
|---|---|
| 1 | B.P. 77,1° C.<br>IR. 3255 (OH); 1651 (C=O)<br>NMR; 7,12–6,67 (m, 1OH, Ar.); 3,53 (s, 2H, CH$_2$-3); 3,37 (s, 2H, —CH$_2$—Py); 2,73 (s, 2H, CH$_2$-1); 1,38 (s, 6H, CH$_3$) |
| 2 | B.P. 160,1° C.<br>IR; 3450 (OH)<br>1620(C=O)<br>NMR; 7,30–6,90 (m, 1OH, Ar.); 3,81 (s, 2H, CH$_3$-3); 3,68 (s, 2H, CH$_2$-Py); 2,93 (s, 3H, CH$_3$—N); 2,85 (s,2H, CH$_2$-1); 1,3 (s, 6H, CH$_3$) |
| 3 | B.P. 178–179° C.<br>IR; 3415 (—NH—), 1689 (—C=O), 1531, 1010 (SO$_2$)<br>NMR; δ = 7,4–7,0 (m, 9H, 2 Ar); 5,42 (b; 1H, —NH); 3,72 (s, 2H, CH$_2$), 3,67 (s; 2H, —CH$_2$—); 2,87 (s, 2H, CH$_2$), 1,30 (s, 6H, 2CH$_3$) |
| 4 | B.P. 187–188° C.<br>IR; 3240, 2955, 1729, 1480, 1449, 1397, 1325, 1180, 1102, 695, 3190, 2955, 1717, 1450, 1400, 1341, 1321, 1170, 1115, 974, 693, 500<br>NMR; δ(ppm); 7,91 (s, 1H, —NH—); 7,32–7,01 (m, 9H, arom); 3,69 (s, 2H, —CH$_2$—N—); 3,67 (s, 2H, CH$_2$—C=O); 3,10 (s, 3H, CH$_3$-s); 2,87 (s, 2H, —CH$_2$—); 1,31 (s, 6H, —CH$_3$) |
| 5 | B.P. 196–197° C.<br>IR; 3480 (—NH—) 1716 (—C=O), 1447 (—SO$_2$—) cm$^{-1}$ 1175, 1131, 1084 (SO$_2$)<br>NMR; δ = 8,3 (s, b NH), 7,9–6,9 (m, 14 H, 3M); 3,55 (s, 4H, 2—CH$_2$—); 2,83 (s, 2H, CH$_2$), 1,26 (s, 6H, 2 CH$_3$) |
| 6 | B.P. 207–209° C.<br>IR; 3295 (—NH—), 1721 (—C=N), 1413, 1183, 1084 (—SO$_2$)<br>NMR; 7,8–7,7 (m, 2H, AA'), 7,35–6,95 (m, 11H, 2 Ar + BB'); 3,55 (5,2H, CH$_2$); 3,54 (s; 2H, CH$_2$); 2,84 (s, 2H; CH$_2$); 2,45 (s, 3H, Ar—CH$_3$); 1,26 (s; 6H; 2—CH$_3$) |
| 7 | B.P. 163° C.<br>IR; 3220, 2950, 1721, 1432, 1395, 1341, 1176, 1113, 971, 878<br>NMR; 7,31–7,14 (m, 5H, arom,); 6,83 + 6,56(AB,2H,J = 3,7Hz—CHCH—); 3,72(s,2H,); 3,69(s, 2H); 3,44(s,3H, —SO$_2$CH$_3$); 2,84(s,2H,—CH$_2$—); 1,30(s,6H,—CH$_3$) |
| 8 | B.P. 188° C.<br>IR; 3235 (—NH—), 1725 (—C=O), 1442, 1166, 1083 (SO$_2$—)<br>NMR; 8,1 (b, 1H,—NH), 7,9–7,8(m,2H,AA',Ar), 7,4–7,1 (m,7H,Ar + BB') 6,74, 2,82(s,2H, CH$_2$); 2,29–2,41 (m,2H,CH$_2$—COOH) (6,45(AB,JAB = 3,75Hz); 3,58 (s,2H,CH$_2$); 3,56(s,2H,CH$_2$) 2,80(s,2H,CH$_2$), 2,45(s,3H,Ar—CH$_3$); 1,25(5,6H;2CH$_3$) |
| 9 | B.P. 191° C.<br>IR; 3435, 3225, 1721, 1598, 1447, 1400, 1340, 1320, 1111, 971<br>NMR; 7,32–7,01 (m, 9H, arom); 3,71 (s, 2H, —CH$_2$—CO-7); 3,68 (s, 2H, ); 3,11 (s, 3H, —SO$_2$—CH$_3$); 2,85 (s, 2H, —CH$_2$—); 1,64 (q, 4H, J = 7,5, ethyl), 0,91 (t, 6H, J = 7,5, ethyl) |
| 10 | IR; 3225 (—NH—), 1721 (—C=O), 1439 (—SO$_2$—) cm$^{-1}$ 1184 ((SO$_2$), 1081 (SO$_2$)<br>NMR; 7,79–6,95 (m, 13H, arom), 3,57 (s, 2H, —CH$_2$—C=O), 3,54 (s, 2H, —CH$_2$—N—), 2,8 (s, 2H,—CH$_2$—), 2,44 (s, 3H, Ph—CH$_3$) |
| 11 | B.P. 140–142° C.<br>IR; 3260 (—NH—), 1722(—C=O), 1437 (—SO$_2$—) 1327, 1113<br>NMR; 7,4–7,1 (m, 5H, Ar); 6,82/6,55 (AB-System, J$_{AB}$ = 3,8 Hz 3,72 (s,2H, CH$_2$); 3,71(s,2H, CH$_2$); 3,21 (s; 3H, SO$_2$CH$_3$), 2,82(s,2H,CH$_2$), 1,619 (q,4H, 2—CH$_2$, J = 7,4Hz; 0,899 (t, 6H, J = 7,4Hz, 2CH$_3$—) |
| 12 | B.P. 158–160° C.<br>IR; 3225 (—NH—), 1721 (—C=O); 1432, 1184, 1084 (—SO$_2$)<br>NMR; 8,02 (b,1H; NH—); 7,9–7,8 (m,2H; AA') 7,4–7,1 (m=,7H, Ar + BB'); 6,740/6,446(AB,2H, JAB = 3,7HZ); 3,58(s,4H, 2—CH$_2$); 2,79 (s,2H,CH$_2$), 2,45(s,3H, Ar—CH$_3$); 1,57 (q,4H;2CH$_2$); 0,861 (t,6H,2CH$_3$) |
| 13 | B.P. 210° C. unter Zersetzung<br>IR; 3300 (NH); 1720 (C=O)<br>NMR; 1,20–1,58 (m, 4H, —CH$_2$—CH$_2$—); 1,26 (s, 6H, CH$_3$); 1,99–2,20 (m, 2H, CH$_2$—CO); 2,42 (s, 3H, Ar—CH$_3$); 2,83 (s, 2H, CH3); 2,28–2,39 (m, 2H, CH$_2$—Py); 3,75 (s, 2H, CH$_2$), 6,94–7,71 (m, 14H, Ar.) |
| 14 | B.P. 203–204° C.<br>IR; 3430, 3175, 3161, 1678, 1596, 1466, 1438, 1341, 1133.<br>NMR; 8,2–7,7 (b, 1H, NH), 7,4–7,1 (m, 5H, Ar,); 6,90 (d, 1H, J = 4,0Hz, thien.), 6,69 (d, 1H, J = 4,0 Hz, thien.); 6,38 (q, 1H, J = 0,8Hz, thiaz.);4,07 (s, 2H, CH$_2$); 3,271 (s, 3H, SO$_2$CH$_3$); 2,554 (d, 3H, J = 0,8Hz). |
| 15 | B.P. >190° C. u.Z.<br>IR; 3480 (CNH); 1722 (C=O)<br>NMR; 7,51–7,08 (m, 9H, Ar); 3,67 (s, 2H, CH$_2$—C); 3,58 (s, 2H, CH$_2$—), 3,07 (s, 3H, CH$_3$); 2,86 (s, 2H, CH$_2$); 1,28 (s, 6H, CH$_2$) |

We claim:

1. A heterocyclic compound of formula I:

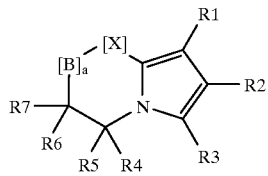

in which two of the radicals R$^1$, R$^2$ and R$^3$, which may the identical or different, stand for a hydrogen atom, a phenyl or naphthyl radical, which optionally has one or two substituents which are selected from the group consisting of halogen, CN, CF$_3$, NO$_2$, OH, alkoxy, OCF$_3$, alkyl and phenyloxy, or for a mono- or bicyclic aromatic heterocyclic radical which has at least one heteroatom selected from the group consisting of oxygen, nitrogen and sulfur and which is optionally condensed with a phenyl or napthyl radical and is optionally substituted by halogen, CF$_3$, alkyl or alkoxy, and the third of the radicals R$^1$, R$^2$ and R$^3$ stands for COCO$_2$H, COCO$_2$ alkyl or A—Y, A stands for C$_1$–C$_8$ alkylene or C$_2$–C$_8$ alkenylene, Y stands for CONR$^8$R$^9$, R$^8$ stands for H, alkyl, OH, or acyl, and R$^9$ is SO$_2$ alkyl, or SO$_2$ phenyl, and the alkyl radical of the sulfonyl group is optionally substituted by one or more halogen atoms and the phenyl radical of the sulfonyl group is optionally substituted by one or more halogen, C$_1$–C$_8$ alkyl, or C$_1$–C$_8$ alkoxy radicals, R$^4$, R$^5$, R$^6$ and R$^7$, which may be identical or different, stand for H or alkyl, or two of the vicinal radicals stand for a chemical bond between the two ring atoms to which they are bonded and the other two have the meanings recited, X stands for CH$_2$, CO, O, S, or NR$^{10}$, where R$^{10}$ stands for H, alkyl or phenyl, which is optionally substituted by halogen, C$_1$–C$_8$ alkyl, or C$_1$–C$_8$ alkoxy, B stands for CH$_2$, and a stands for 0, and their salts and esters.

2. The compound of claim 1 of formula I, in which two of the radicals $R^1$, $R^2$ and $R^3$, independently of one another, stand for a hydrogen atom, a phenyl radical, a phenyl radical substituted by one or two halogen atoms or $CF_3$ or a 5- or 6-membered aromatic heterocyclic radical, which as defined in claim 1 is optionally substituted and condensed, the third of the radicals $R^1$, $R^2$ and $R^3$ stands for A—Y, wherein A stands for $C_1$–$C_8$ alkylene, and Y has the meanings recited in claim 1.

3. The compound of claim 2 of formula I, wherein $R^1$ stands for H or phenyl, $R^2$ for phenyl, halogen- or $CF_3$-substituted phenyl, thienyl, halogen-substituted thienyl, or furanyl.

4. The compound of claim 1, wherein $R^9$ stands for $SO_2CF_3$, $SO_2CH_3$, $SO_2$ phenyl, or $SO_2$ tolyl.

5. [6-(4-Trifluoromethylphenyl)-2,2-dimethyl-7-phenyl-2,3-dihydro-1H-pyrrolizin-5-yl] acetic acid methane sulfonamide.

6. A pharmaceutical composition containing at least one compound of claim 1, optionally in combination with pharmaceutically compatible vehicle and/or additive substances.

7. A process for preparing the compounds of claim 1, wherein a compound of the general formula II:

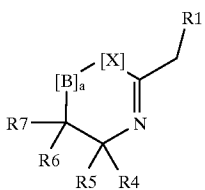

is reacted with a compound of the general formula III:

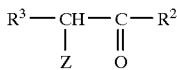

wherein in the above formulas the radicals B, a, X and $R^1$–$R^7$ have the meanings recited in claim 1 and Z stands for Cl or Br, to form a compound of the general formula Ia:

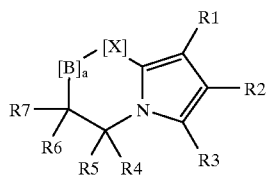

in which $R^1$–$R^7$, B, a and X have the meanings recited in claim 1 and into the compound obtained, the radical A—$CO_2H$ is inserted and the acid obtained is converted into the desired sulfonamide, amide or imide.

8. The process of claim 7, wherein a compound of formula Ia in which one of the radicals $R^1$, $R^2$ and $R^3$ stands for A—$CO_2H$, is reacted in the form of an activated derivative with the corresponding sulfonamide, amide or imide, optionally in the presence of a base.

9. The process of claim 7, for preparing the formula I compounds, in which the third of the radicals $R^1$, $R^2$ and $R^3$ stands for $CH_2COOH$, wherein a compound of formula Ia defined in claim 7 is a) reacted with oxalyl chloride to form a compound of formula I, in which one of the radicals $R^1$, $R^2$ and $R^3$ stands for $COCO_2H$, and this compound is treated with a reagent which is suitable for reducing the keto group of the ketocarboxylic acid to a $CH_2$ group, b) reacted with a diazoethanoic acid alkyl ester to form a formula I compound, in which one of the radicals $R^1$, $R^2$ and $R^3$ stands for $CH_2COO$ alkyl and the compound obtained is subjected to ester cleavage, or c) is reacted with chloral to form a formula I compound, in which one of the radicals $R^1$, $R^2$, and $R^3$ stands for —CH(OH)$CCl_3$ and the compound obtained is converted into an activated derivative, which is reduced with dithionite.

* * * * *